United States Patent
Kuroda

(10) Patent No.: US 8,496,891 B2
(45) Date of Patent: Jul. 30, 2013

(54) REACTION CONTAINER HOLDER AND ANALYZER

(75) Inventor: Chikara Kuroda, Shizuoka (JP)

(73) Assignee: Beckman Coulter, Inc., Brea, CA (US)

( * ) Notice: Subject to any disclaimer, the term of this patent is extended or adjusted under 35 U.S.C. 154(b) by 0 days.

(21) Appl. No.: 13/202,571

(22) PCT Filed: Mar. 2, 2010

(86) PCT No.: PCT/JP2010/053348
§ 371 (c)(1),
(2), (4) Date: Aug. 19, 2011

(87) PCT Pub. No.: WO2010/103960
PCT Pub. Date: Sep. 16, 2010

(65) Prior Publication Data
US 2011/0311397 A1    Dec. 22, 2011

(30) Foreign Application Priority Data

Mar. 9, 2009    (JP) .................................. 2009-055559

(51) Int. Cl.
*B01L 9/00*  (2006.01)
*B01L 3/14*  (2006.01)
*G01N 21/00* (2006.01)
*G01N 31/00* (2006.01)
*G01N 33/00* (2006.01)

(52) U.S. Cl.
USPC ............................. 422/560; 422/64; 422/549

(58) Field of Classification Search
USPC ...... 422/63–64, 82.05, 522, 560–561; 73/863
See application file for complete search history.

(56) References Cited

U.S. PATENT DOCUMENTS 4,056,361 A * 11/1977 Peters et al. .................... 422/64
6,558,632 B1 * 5/2003 Guller et al. .................. 422/560
(Continued)

FOREIGN PATENT DOCUMENTS

JP    58-127360 U    8/1983
JP    60-105967 A    6/1985
(Continued)

OTHER PUBLICATIONS

International Search Report from PCT/JP2010/053348, mailed May 25, 2010, included English Translation, 2 pages.
(Continued)

*Primary Examiner* — Jill Warden
*Assistant Examiner* — Julie Tavares
(74) *Attorney, Agent, or Firm* — Kilpatrick Townsend & Stockton LLP

(57) ABSTRACT

A reaction container holder capable of inhibiting the lowering of the transfer efficiency of heat transferred from a rotating member to a bottom surface of a reaction container, and an analyzer comprising the reaction container holder, are provided. In a reaction container holder comprising: a retaining member unit comprising a plurality of container retaining sections for retaining reaction containers, which house a reaction liquid containing a reagent and a specimen; and a circular rotating member for detachably fixing the unit from above and rotating, the holder keeping the container at a constant temperature by transferring heat from a heat source through the rotating member to the container, the rotating member comprises a level difference section, an upper surface of which is positioned below a bottom surface of the container retained by the unit and above a bottom part of the section, when the retaining member unit is fixed.

6 Claims, 5 Drawing Sheets

U.S. PATENT DOCUMENTS

2004/0265173 A1* 12/2004 Matsumoto et al. ............ 422/64
2009/0191094 A1* 7/2009 Kayahara et al. ............... 422/64

FOREIGN PATENT DOCUMENTS

| | | |
|---|---|---|
| JP | 1-150858 A | 6/1989 |
| JP | 2008-58250 A | 3/2008 |
| WO | WO 2007135921 A1 * | 11/2007 |

OTHER PUBLICATIONS

International Search Report from PCT/JP2010/053348, mailed May 25, 2010, included English Translation, 2 pages (previously cited Aug. 19, 2011).

* cited by examiner

REACTION CONTAINER HOLDER AND ANALYZER

CROSS-REFERENCE TO RELATED APPLICATION

This application is a National Stage of International Application No. PCT/JP2010/053348, filed Mar. 2, 2010, which claims the benefit of priority to Japanese Application No. 2009-055559, filed Mar. 9, 2009, the disclosures of each are herein incorporated by reference.

TECHNICAL FIELD

The present invention relates to: a reaction container holder for keeping a plurality of reaction containers at a constant temperature, each reaction container housing a reaction liquid of a reagent and a specimen; and an analyzer comprising the reaction container holder.

BACKGROUND ART

Conventionally, analyzers analyze a specimen by optically measuring a reaction liquid obtained by reaction between a specimen and a reagent while keeping the reaction liquid at a temperature as high as a human's body temperature. To that end, the analyzers include a reaction container holder which rotates while keeping a plurality of reaction containers for housing a reaction liquid at a constant temperature (see Patent Literature 1, for example). As for such a reaction container holder, it is known to include a retaining member having a plurality of retaining sections for retaining reaction containers, and a circular rotating member for detachably fixing the retaining member from above and rotating, where the retaining member can be removed from the rotating member for the cleaning of the retaining member.

CITATION LIST

Patent Literature

Patent Literature 1: Japanese Laid-Open Publication No. 2008-58250

DISCLOSURE OF THE INVENTION

Summary of Invention

Technical Problem

In the conventional reaction container holder having the retaining member and the rotating member above, however, the reaction container is retained by the empty retaining member, and subsequently, the retaining member is attached and fixed to the rotating member. As a result, there may be a case where there is a gap produced between a bottom surface of the reaction container and the rotating member depending on a state of the reaction container being retained by the retaining member, or depending on a fixed state of the retaining member in relation to the rotating member. When there is produced such a gap, a problem arises where the transfer efficiency of the heat transferred from the rotating member to the bottom surface of the reaction container is lowered.

The present invention is intended to solve such a problem as described above. It is an objective of the present invention to provide: a reaction container holder capable of inhibiting the lowering of the transfer efficiency of the heat transferred from the rotating member to the bottom surface of the reaction container; and an analyzer comprising the reaction container holder.

Solution to Problem

A reaction container holder according to the present invention comprises: a retaining member comprising a plurality of retaining sections for retaining reaction containers, the reaction container housing a liquid sample containing a reagent and a specimen; and a circular rotating member for detachably fixing the retaining member from above and rotating, the reaction container holder keeping the reaction container at a constant temperature by transferring heat from a heat source through the rotating member to the reaction container, and the reaction container holder is characterized in that the rotating member comprises a level difference section, where an upper surface of a level difference is positioned above a bottom part of the retaining section within the retaining section when the retaining member is fixed, thereby solving the problem and achieving the objective as described above.

In the invention described above, the reaction container holder according to the present invention is characterized in that the level difference section is a convex portion formed at the outer edge of the rotating member along the circumferential direction, and engages with the retaining section when the retaining member is fixed to the rotating member.

In the invention described above, the reaction container holder according to the present invention is characterized in that the level difference section is formed in a trapezoidal pyramid, or a trapezoidal cone, with a narrowing upper part.

In the invention described above, the reaction container holder according to the present invention is characterized in that the retaining section comprises a protruding piece, which is a downward protrusion of a side wall on an outer periphery side thereof, and the protruding piece fits tightly with the level difference section when the retaining member is fixed to the rotating member.

In the invention described above, the reaction container holder according to the present invention is characterized in that the level difference section comprises an elastic heat transferring material coated on an upper surface of the level difference thereof.

An analyzer according to the present invention for measuring optical properties of a reaction liquid of a reagent and a specimen housed in the reaction container, to analyze the reaction liquid is characterized in that the analyzer optically analyzes the reaction liquid by using the reaction container holder according to the present invention, thereby solving the problem and achieving the objective as described above.

Advantageous Effects of Invention

According to the present invention, in a reaction container holder comprising: a retaining member comprising a plurality of retaining sections for retaining reaction containers, the reaction container housing a liquid sample containing a reagent and a specimen; and a circular rotating member for detachably fixing the retaining member from above and rotating, the reaction container holder keeping the reaction container at a constant temperature by transferring heat from a heat source through the rotating member to the reaction container, the rotating member comprises a level difference section, where an upper surface of a level difference is positioned above a bottom part of the retaining section within the retaining section when the retaining member is fixed. As a result, even if the bottom surface of the reaction container is retained at a position higher than the bottom part of the retaining section, or even if the bottom part of the retaining section is fixed at a position higher than a predetermined position with respect to the rotating member, the gap produced between the bottom part of the reaction container and the rotating member can be reduced, thereby inhibiting the lowering of the transfer efficiency of the heat transferred from the rotating member to the bottom surface of the reaction container.

BEST MODE FOR CARRYING OUT THE INVENTION

Hereinafter, preferred Embodiments of a reaction container holder and an analyzer according to the present invention will be described in detail with reference to the accompanying drawings. It should be noted that the present invention will not be limited to the Embodiments as set forth herein.

Figure 1:
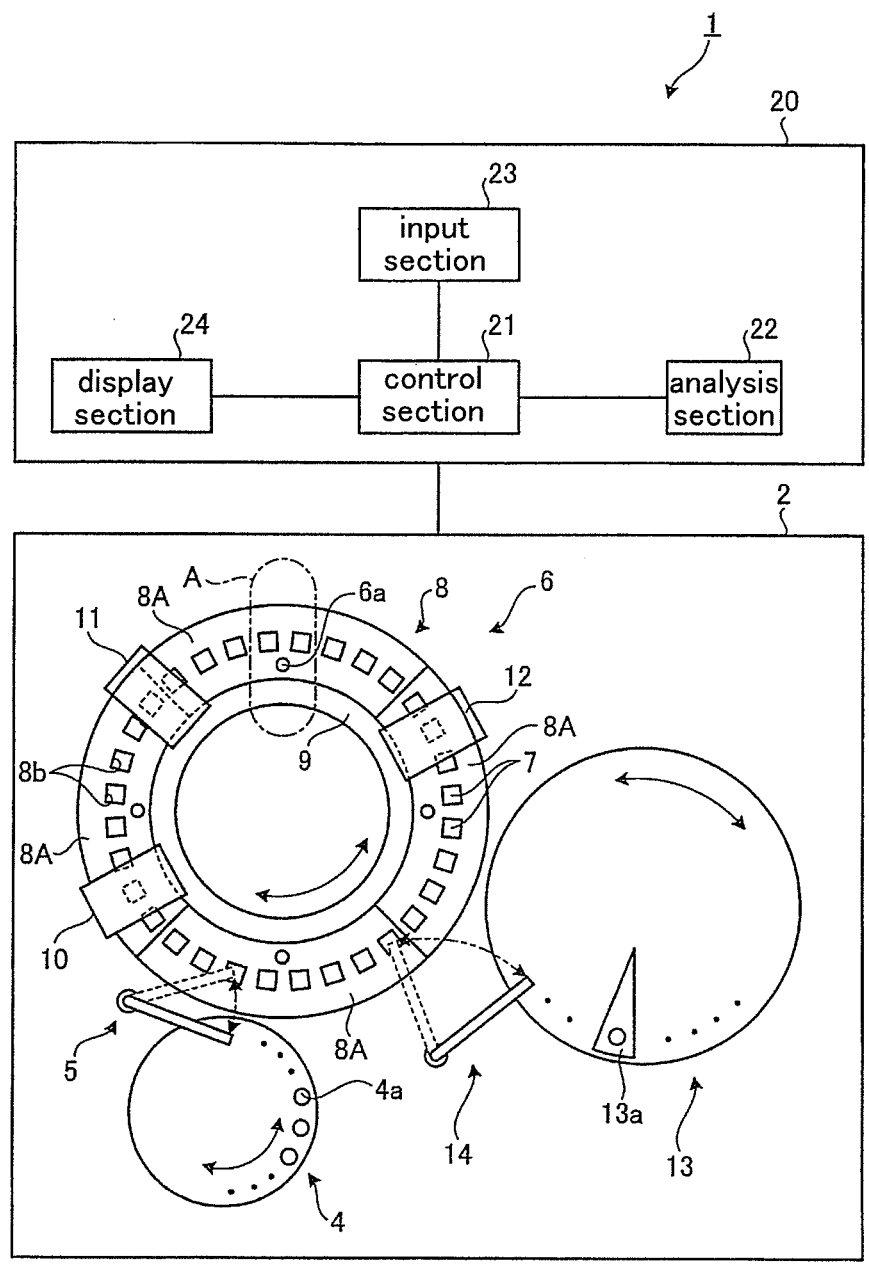
FIG. 1 is a schematic view illustrating a configuration of an analyzer according to Embodiments of the present invention.

FIG. 1 is a schematic view illustrating a configuration of an analyzer according to the Embodiments of the present invention. An analyzer 1 according to the Embodiments includes a measuring section 2 and a control apparatus 20. The measuring section 2 dispenses each of a specimen and a reagent into a reaction container 7, and optically measures a reaction caused in the reaction container 7. The control apparatus 20 performs the overall control of the analyzer 1 including the measuring section 2, and analyzes a measurement result in the measuring section 2.

The measuring section 2 includes a specimen table 4, a specimen dispensing mechanism 5, a reaction container holder 6, a stirring apparatus 10, a photometry apparatus 11, a washing apparatus 12, a reagent table 13 and a reagent dispensing mechanism 14.

The specimen table 4 is rotated in the direction of the arrow by a driving means (not shown), and a specimen container 4a having a specimen housed therein is detachably stored in the specimen table 4.

The specimen dispensing mechanism 5 is a means for dispensing a specimen into a plurality of reaction containers 7 retained in the reaction container holder 6, and the specimen dispensing mechanism 5 dispenses a specimen from a plurality of specimen containers 4a of the specimen table 4 successively into the reaction containers 7.

The reaction container holder 6 is rotated in the direction of the arrow by a driving means (not shown), and the reaction container holder 6 retains and keeps a plurality of reaction containers 7 at a constant temperature to keep a liquid sample, containing a reagent and a sample, dispensed into the reaction containers 7 at a constant temperature. The reaction container holder 6 includes a retaining member 8 and a rotating member 9.

The retaining member 8 consists of a plurality of retaining member units 8A, each retaining member unit 8A being detachably fixed along the circumferential direction of the rotating member 9 by a screw 6a. The retaining member unit 8A includes a plurality of container retaining sections 8b for retaining the reaction containers 7 of a substantially rectangular parallelepiped shape.

Figure 2:
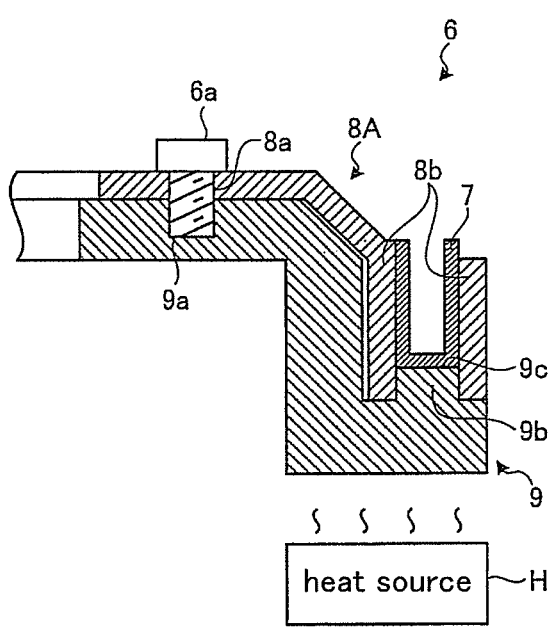
FIG. 2 is an enlarged cross sectional view of a part A of a reaction container holder illustrated in FIG. 1.

The rotating member 9 is a circular member which is rotated by a driving mechanism (not shown), with a vertical line along the center of the reaction container holder 6 as an axis of rotation. The rotating member 9 includes a level difference section 9b, as illustrated in FIG. 2. The level difference section 9b is a convex portion of a substantially rectangular parallelepiped shape formed at the outer edge of the rotating member 9 along the circumferential direction. With regard to an upper surface 9c of the level difference section 9b, when the retaining member unit 8A is fixed, the upper surface 9c of a level difference is positioned within the container retaining section 8b and above the bottom part of the container retaining section 8b. A heat source H is provided below the rotating member 9. Heat generated from the heat source H is transferred to the reaction container 7 through the rotating member 9.

The stirring apparatus 10 stirs a liquid sample containing a reagent and a specimen housed in a reaction container 7.

The photometry apparatus 11 includes a light source for emitting analysis light, the analysis light being for analyzing a reaction liquid obtained by reaction between a specimen and a reagent housed in a reaction container 7, and a light receiver for separating and receiving the analysis light, which is transmitted through the reaction liquid. The photometry apparatus 11 measures optical properties of the reaction liquid in the reaction container 7 and outputs a measurement result thereof to the control apparatus 20.

The washing apparatus 12 washes inside the reaction container 7 which has finished the measurement performed by the photometry apparatus 11.

The reagent table 13 is rotated in the direction of the arrow by a driving means (not shown), and a reagent container 13a housing a reagent is detachably stored therein.

The reagent dispensing mechanism 14 is a means for dispensing a reagent into a plurality of reaction containers 7 retained by the reaction container holder 6, and the reagent dispensing mechanism 14 dispenses a reagent from a given reagent container 13a of the reagent table 13 successively into reaction containers 7.

The control apparatus 20 includes a control section 21, an analysis section 22, an input section 23 and a display section 24. The control section 21 is connected with the measuring section 2 and the respective sections described above within the control apparatus 20, and is effectuated by a microcomputer or the like. The control section 21 controls the operation of respective sections of the analyzer 1.

The analysis section 22 analyzes concentration of components of a specimen or the like on the basis of optical properties of a reaction liquid in a reaction container 7 measured by the photometry apparatus 11, and outputs an analysis result to the control section 21. The input section 23 is an operation section for performing operations of inputting an examination menu to the control section 21. For example, the input section 23 is effectuated by a keyboard, a mouse or the like. The display section 24 displays analysis content, analysis results, warning or the like, and the display section 24 is effectuated by a display panel or the like.

In the analyzer 1 as configured above, the reagent dispensing mechanism 14 successively dispenses a reagent from the reagent container 13a into the plurality of reaction containers 7 transported along the circumferential direction by the rotating reaction container holder 6. The reaction containers 7 with the dispensed reagent therein are transported by the reaction container holder 6 along the circumferential direction thereof, and the reaction containers 7 are successively dispensed with a specimen by the specimen dispensing mechanism 5 from a plurality of specimen containers 4a retained to the specimen table 4. Subsequently, the reaction containers 7 with the specimen dispensed therein are conveyed to the stirring apparatus 10 by the reaction container holder 6, and the dispensed reagent and specimen are successively stirred and they react with each other. The reaction containers 7 housing the reaction liquid, which is obtained by the reaction between the specimen and the reagent as described above, pass through the photometry apparatus 11 as the reaction container holder 6 rotates again, and analysis light emitted from the light source transmits the reaction containers. The analysis light that has transmitted the reaction liquid is measured with regard to optical properties, and concentration of the components or the like is analyzed by the analysis section 22. The reaction containers 7 which have finished with the analysis are washed by the washing apparatus 12. The analyzer 1 successively performs such a series of analysis operations.

Figure 3:
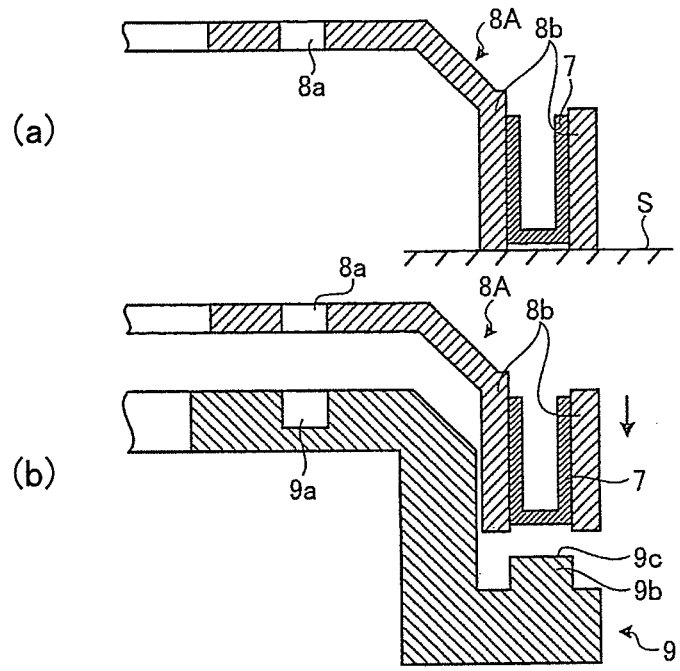
FIG. 3 is a diagram describing procedures for fixing a retaining member unit to a rotating member illustrated in FIG. 1.
Figure 4:
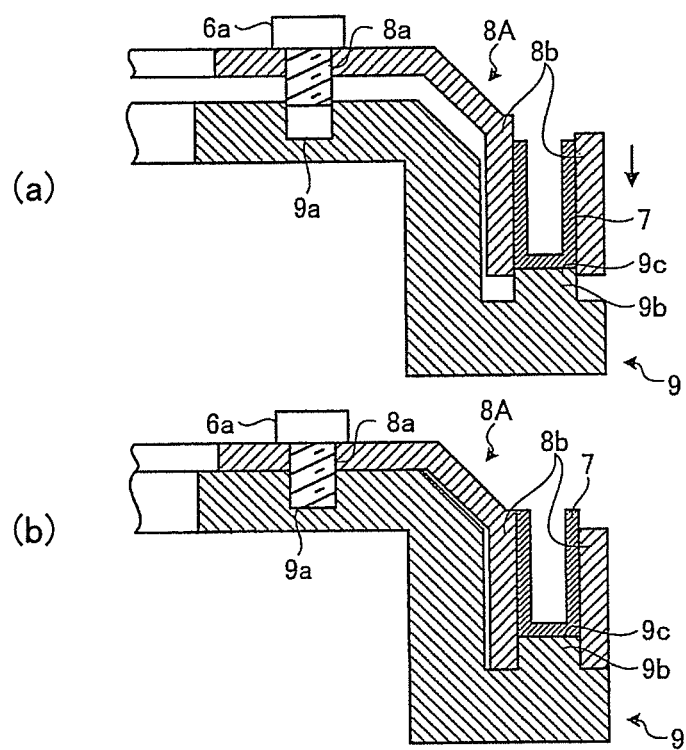
FIG. 4 is a diagram describing procedures for fixing a retaining member unit to a rotating member illustrated in FIG. 1.

Next, procedures of an operator fixing the retaining member unit 8A to the rotating member 9 will be described with reference to FIGS. 3 and 4. First, the operator inserts reaction containers 7 into each of a plurality of container retaining sections 8b, allowing the retaining member units 8A to be upright on a flat working plane S, such as a desk. As a result, the reaction containers 7 are retained by the retaining member unit 8A in such a manner that the bottom surfaces of the reaction containers 7 are positioned near the bottom part of the container retaining sections 8b (see FIG. 3 (a)). The reaction containers 7 may also be retained such that the bottom surfaces of the reaction containers 7 are retained at a position above the bottom part of the container retaining sections 8b, as illustrated in FIG. 3 (a). Subsequently, the retaining member unit 8A is assembled into the rotating member 9 from above such that the container retaining section 8b is engaged with the level difference section 9b (see FIG. 3 (b)).

Next, the operator begins to screw the screw 6a tight. As a result, the retaining member unit 8A begins to descend towards a position where the retaining member unit 8A is to be fixed with the rotating member 9, and during the descending, the upper surface 9c of the level difference section 9b touches the bottom surface of the reaction container 7 (see FIG. 4 (a)). As illustrated in FIG. 4 (a), the level difference section 9b engages with the container retaining sections 8b such that the upper surface 9c is positioned above the bottom part of the container retaining sections 8b. Thus, even if the reaction container 7 is retained in such a manner that the bottom surface thereof is positioned above the bottom part of the container retaining sections 8b, the upper surface 9c of the level difference section 9b touches the bottom surface of the reaction container 7. Subsequently, together with the tight screwing of the screw 6a, the retaining member unit 8A descends while leaving the reaction container 7 on the upper surface 9c of the level difference section 9b. When the resistance against the screwing of the screw 6a increases, the retaining member unit 8A is fixed to the rotating member 9 (see FIG. 4 (b)).

In the present Embodiment, when the retaining member unit 8A is fixed to the rotating member 9, the upper surface 9c of the level difference section 9b is positioned above the bottom part of the container retaining sections 8b within the container retaining sections 8b. Accordingly, even if the bottom surface of the reaction container 7 is retained at a position higher than the bottom part of the container retaining sections 8b, or even if the bottom part of the container retaining sections 8b is fixed at a position higher than a predetermined position with respect to the rotating member 9, the occurrence of the gap between the bottom part of the reaction container 7 and the rotating member 9 can be reduced. Therefore, the lowering of the transfer efficiency of the heat transferred from the rotating member 9 to the bottom surface of the reaction container 7 can be inhibited.

In addition, in the present Embodiment, since the retaining member unit 8A is fixed to the rotating member 9 by engaging the container retaining sections 8b with the level difference section 9b, the retaining member 8 can be fixed at a correct position with respect to the rotating member 9.

Variation Example 1

Figure 5:
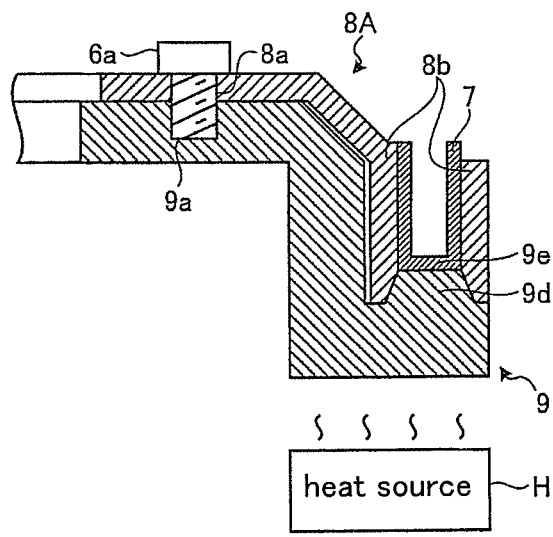
FIG. 5 is a diagram describing Variation Example 1 of a reaction container holder illustrated in FIG. 1.

Variation Example 1 of the Embodiments will be described hereinafter. In Variation Example 1, the level difference section of the rotating member 9 is formed, for example, in a trapezoidal pyramid with a narrowing upper part, as the level difference section 9d illustrated in FIG. 5. In such a level difference section 9d, the container retaining sections 8b and the level difference section 9d engage with each other by being guided by the inclined side surface of the level difference section 9d, making it possible to engage the container retaining sections 8b with the level difference section 9d with ease. The level difference section 9d may also be a trapezoidal cone with a narrowing upper part.

Variation Example 2

Figure 6:
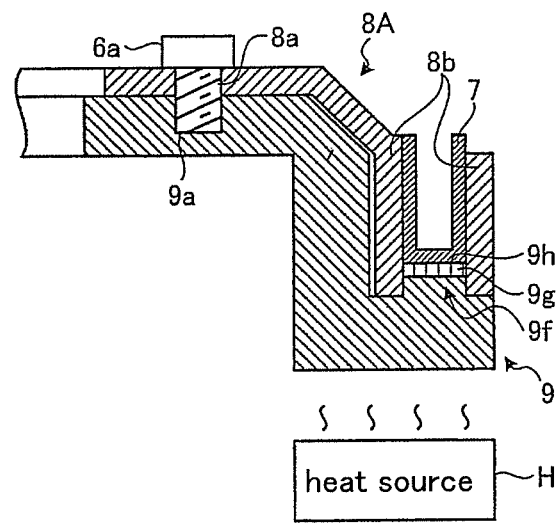
FIG. 6 is a diagram describing Variation Example 2 of a reaction container holder illustrated in FIG. 1.

Next, Variation Example 2 of the Embodiments will be described hereinafter. In Variation Example 2, the level difference section of the rotating member 9 is, for example, such that an upper surface 9h of a level difference section 9f is coated with an elastic heat transferring material 9g, as the level difference section 9f illustrated in FIG. 6. The heat transferring material 9g may also coat the upper surface 9h of the level difference section 9f, with an adhesive having heat conductivity. Alternatively, the heat transferring material 9g itself may also be adhered directly to the upper surface 9h of the level difference section 9f. In this case, when the upper surface 9h of the level difference section 9f touches the bottom surface of the reaction container 7, the heat transferring material 9g is elastically deformed. As a result, the bottom surface of the reaction container 7 can be adhered to the level difference section 9f even better.

Variation Example 3

Figure 7:
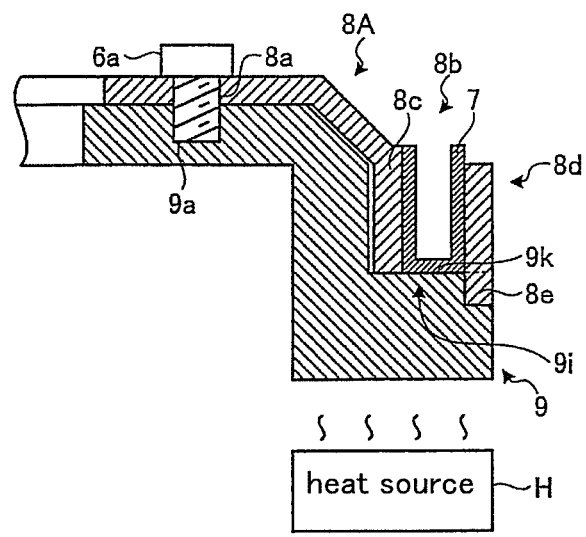
FIG. 7 is a diagram describing Variation Example 3 of a reaction container holder illustrated in FIG. 1.

Next, Variation Example 3 of the Embodiments will be described hereinafter. In Variation Example 3, a container retaining section 8b of a retaining member unit 8A includes a protruding piece 8e as illustrated in FIG. 7. The protruding piece 8e is a protruding portion of the lower part of a side wall 8d, which is the one closer to the outer periphery between the side walls 8c and 8d opposing with each other in a horizontal direction. When a reaction container 7 is inserted in a container retaining section 8b of the retaining member unit 8A removed from the rotating member 9, the reaction container 7 is retained by the retaining member unit 8A in such a manner that the bottom surface of the reaction container 7 is positioned near the bottom part of the protruding piece 8e. When the retaining member unit 8A is fixed to the rotating member 9, the protruding piece 8e fits tightly together with a level difference section 9i. As a result, an upper surface 9k of the level difference section 9i is positioned above the bottom part of the protruding piece 8e within the container retaining sections 8b. Therefore, even if the reaction container 7 is retained in such a manner that the bottom surface of the reaction container 7 is retained at a position higher than the bottom part of the protruding piece 8e, or even if the retaining member unit 8A is fixed in such a manner that the bottom portion of the protruding piece 8e is positioned higher than a predetermined position with respect to the rotating member 9, the occurrence of a gap between the bottom part of the reaction container 7 and the rotating member 9 can be reduced.

In the present embodiment, while the retaining member 8 is exemplified as consisting of a plurality of retaining member units 8A, the retaining member 8 may also be a single unit.

DESCRIPTION OF THE REFERENCE NUMERALS 1 analyzer
2 measuring section
4 specimen table
5 specimen dispensing mechanism
6 reaction container holder
6a screw
7 reaction container
8 retaining member
8A retaining member unit
8a, 9a threaded hole
8b container retaining section
8c, 8d wall
8e protruding piece
9 rotating member
9b, 9d, 9f, 9i level difference section
9c, 9e, 9h, 9k surface
10 stirring apparatus
11 photometry apparatus
12 washing apparatus
13 reagent table
13a reagent container
14 reagent dispensing mechanism
20 control apparatus
H heat source

The invention claimed is:

1. A reaction container holder comprising:
a retaining member comprising a plurality of retaining sections for retaining reaction containers, the plurality of retaining sections having protruding portions of the retaining member and being irremovable from the retaining member, the reaction container being separate from the retaining sections and housing a liquid sample containing a reagent and a specimen; and
a circular rotating member for detachably fixing the retaining member from above and rotating,
the reaction container holder keeping the reaction container at a constant temperature by transferring heat from a heat source through the rotating member to the reaction container, characterized in that
the rotating member comprises a level difference section, where an upper surface of the level difference section is positioned above a bottom part of the protruding portions within the plurality of retaining sections when the retaining member is fixed.

2. The reaction container holder according to claim 1, characterized in that the level difference section is a convex portion formed at the outer edge of the rotating member along the circumferential direction, and engages with the retaining section when the retaining member is fixed to the rotating member.

3. The reaction container holder according to claim 2, characterized in that the level difference section is formed in a trapezoidal pyramid, or a trapezoidal cone, with a narrowing upper part.

4. The reaction container holder according to claim 1, characterized in that the plurality of retaining sections having protruding portions comprise protruding pieces, which are downward protrusions of a side wall on an outer periphery side thereof, and the protruding pieces fitting tightly with the level difference section when the retaining member is fixed to the rotating member.

5. The reaction container holder according to claim 1, characterized in that the level difference section comprises an elastic heat transferring material coated on the upper surface of the level difference section.

6. An analyzer for measuring optical properties of a reaction liquid of a reagent and a specimen housed in the reaction container, to analyze the reaction liquid, characterized in that the analyzer comprises the reaction container holder according to claim 1, and a photometry apparatus including a light source and a light receiver, wherein light is transmitted through the reaction container to the light receiver, wherein the photometry apparatus is configured to optically analyze the reaction liquid in the reaction container holder and output a measurement result thereof.

* * * * *